(12) United States Patent
Benner et al.

(10) Patent No.: US 9,947,204 B2
(45) Date of Patent: *Apr. 17, 2018

(54) VALIDATION OF MECHANICAL CONNECTIONS

(71) Applicant: International Business Machines Corporation, Armonk, NY (US)

(72) Inventors: Alan F. Benner, Poughkeepsie, NY (US); Benjamin V. Fasano, New Windsor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/501,279

(22) Filed: Sep. 30, 2014

(65) Prior Publication Data

US 2016/0163176 A1 Jun. 9, 2016

Related U.S. Application Data

(63) Continuation of application No. 13/746,207, filed on Jan. 21, 2013, now Pat. No. 8,981,961.

(51) Int. Cl.
*G08C 17/00* (2006.01)
*G08B 21/18* (2006.01)
*H01R 13/641* (2006.01)

(52) U.S. Cl.
CPC ........... *G08B 21/18* (2013.01); *H01R 13/641* (2013.01)

(58) Field of Classification Search
CPC ...... G02B 6/3898; G08B 21/00; G08B 21/18; H01R 13/641

(Continued)

(56) References Cited

U.S. PATENT DOCUMENTS 4,136,256 A * 1/1979 Shepherd ............ C07C 17/2632
540/607
4,136,266 A 1/1979 Cohen et al.
(Continued)

FOREIGN PATENT DOCUMENTS

EP 001136860 A2 9/2001
EP 1833032 A1 9/2007
(Continued)

OTHER PUBLICATIONS

Childers, et al.; "Miniature Detachable Photonic Turn Connector for Optical Module Interface", 2011 Electronic Components and Technology Conference, pp. 1922-1927.

(Continued)

*Primary Examiner* — Amine Benlagsir
(74) *Attorney, Agent, or Firm* — Cantor Colburn LLP; Steven Chiu (57) ABSTRACT

A connection validation apparatus includes a connector engagement mechanism configured to physically engage a connector to connect the connector to a connector interface. The apparatus further includes a connection indication detector located on the connector engagement mechanism and configured to detect at least one of a sound and a vibration corresponding to a secure connection of the connector with the connector interface. The apparatus also includes a connection indicator output unit configured to provide an indication to a user that the connector is securely connected with the connector interface based on the detection of the at least one of the sound and the vibration by the connection indication detector.

6 Claims, 4 Drawing Sheets

(58) Field of Classification Search
USPC .............................................. 340/540, 870.1
See application file for complete search history.

(56) References Cited

U.S. PATENT DOCUMENTS

| | | | |
|---|---|---|---|
| 4,496,213 A | 1/1985 | Borsuk | |
| 4,892,490 A * | 1/1990 | Tsuchiya | H01R 13/641 439/345 |
| 5,203,718 A * | 4/1993 | Chishima | H01R 13/641 439/350 |
| 5,308,251 A * | 5/1994 | Kaufman | G06K 7/0047 439/108 |
| 5,308,261 A * | 5/1994 | Kightlinger | H01R 13/6272 439/352 |
| 6,249,960 B1 * | 6/2001 | Faesel | H01R 43/22 29/750 |
| 6,462,668 B1 * | 10/2002 | Foseide | G08B 13/1418 200/61.59 |
| 6,793,399 B1 | 9/2004 | Nguyen et al. | |
| 6,931,193 B2 | 8/2005 | Barnes et al. | |
| 7,020,376 B1 * | 3/2006 | Dang | B25B 9/02 385/135 |
| 7,534,128 B2 * | 5/2009 | Caveney | H01R 43/26 29/764 |
| RE42,094 E | 2/2011 | Barnes et al. | |
| 7,883,276 B2 * | 2/2011 | Davidson | G02B 6/3813 385/53 |
| 9,103,996 B2 * | 8/2015 | Lin | G02B 6/3898 |
| 2005/0077908 A1 * | 4/2005 | Fessenden | G01R 1/0425 324/543 |
| 2005/0085737 A1 * | 4/2005 | Levia | G01H 3/00 600/528 |
| 2006/0046576 A1 | 3/2006 | Gannon | |
| 2006/0143455 A1 * | 6/2006 | Gitzinger | H04L 63/04 713/170 |
| 2006/0286856 A1 | 12/2006 | Rikio | |
| 2007/0230962 A1 * | 10/2007 | Fisher | G08C 17/02 398/106 |
| 2009/0023329 A1 | 1/2009 | Mehnert | |
| 2009/0226140 A1 * | 9/2009 | Belenkiy | G02B 6/3898 385/134 |
| 2009/0317074 A1 | 12/2009 | Serin et al. | |
| 2010/0302033 A1 * | 12/2010 | Devenyi | H04R 1/1041 340/540 |
| 2011/0001961 A1 * | 1/2011 | Escuin Garcia | G08B 13/1445 356/229 |
| 2011/0019962 A1 * | 1/2011 | Childers | G02B 6/3869 385/76 |
| 2014/0148808 A1 * | 5/2014 | Inkpen | G01B 7/003 606/80 |

FOREIGN PATENT DOCUMENTS

| | | | | |
|---|---|---|---|---|
| FR | 2804507 A1 | 8/2001 | | |
| JP | 02006020121 A | 1/2000 | | |
| JP | 02001039304 A | 2/2000 | | |
| JP | 2005011551 A | * | 1/2005 | G08B 21/18 |
| JP | 2007314925 A | 12/2007 | | |

OTHER PUBLICATIONS

Li, et al.; "Guided Wave and Damage Detection in Composite LaminatesUsing Different Fiber Optic Sensors"; Sensors, 2009; pp. 4005-4021.

* cited by examiner

VALIDATION OF MECHANICAL CONNECTIONS

DOMESTIC PRIORITY

This application is a continuation of U.S. patent application Ser. No. 13/746,207, filed Jan. 21, 2013, the disclosure of which is incorporated by reference herein in its entirety.

STATEMENT REGARDING FEDERALLY SPONSORED RESEARCH OR DEVELOPMENT

This invention was made with government support under contract number HR0011-07-9-0002 awarded by Defense Advanced Research Projects Agency (DARPA). The Government has certain rights to this invention.

BACKGROUND

The present disclosure relates to validating mechanical connections, and in particular to detecting sound or vibration indicating a secure connection of a mechanical connector with a connector interface.

Assembling optically-interconnected clusters or switched-fabric systems requires the actuation of large arrays of optical fiber connectors, such as multi-fiber push-on/pull-off (MTP/MPO) connectors. Each connecting process requires applying sufficient force to mechanically engage a spring mechanism that indicates a successful engagement. In MTP/MPO connectors, for example, spring-loaded elements press optical fiber interfaces together and maintain the contact between the interfaces during testing, shipping and use. Other connectors, such as Ethernet cables or telephone cables, may also include spring mechanisms, such as bendable tabs that may lock the connector into a receptacle.

Each connector indicates a full engagement by producing a "click" sound. However, in noisy environments, such as in a manufacturing or data center environment, the sound may be difficult to detect. In addition, when many connections need to be made in an array, and when the connectors are densely-packed, discerning individual connector engagements may be very difficult and may result in partial engagements, rather than full and secure engagements.

SUMMARY

Exemplary embodiments include a connection validation apparatus. The apparatus includes a connector engagement mechanism configured to physically engage a connector to connect the connector to a connector interface. The apparatus further includes a connection indication detector located on the connector engagement mechanism and configured to detect at least one of a sound and a vibration corresponding to a secure connection of the connector with the connector interface. The apparatus also includes a connection indicator output unit configured to provide an indication to a user that the connector is securely connected with the connector interface based on the detection of the at least one of the sound and the vibration by the connection indication detector.

Additional exemplary embodiments include a method of validating a connection. The method includes connecting a connector to a connector interface using a connection apparatus controlled by a user and detecting, by a connection indication detector on the connection apparatus, a connection validation sound generated by the connector based on the connector being connected to the connector interface. The method also includes transforming, by the connection indication detector, the connection validation sound to generate a transformed connection validation sound and generating at least one of an audio, a visual, and a tactile output to a user based on the transformed connection validation sound.

Additional features and advantages are realized by implementation of embodiments of the present disclosure. Other embodiments and aspects of the present disclosure are described in detail herein and are considered a part of the claimed invention. For a better understanding of the embodiments, including advantages and other features, refer to the description and to the drawings.

BRIEF DESCRIPTION OF THE SEVERAL VIEWS OF THE DRAWINGS

The subject matter which is regarded as encompassing embodiments of the present disclosure is particularly pointed out and distinctly claimed in the claims at the conclusion of the specification. The forgoing and other features, and advantages of the embodiments are apparent from the following detailed description taken in conjunction with the accompanying drawings in which:

DETAILED DESCRIPTION

When connector interfaces are engaged, a secure engagement may be detected based on detecting a "click" sound of a spring mechanism. Disclosed embodiments relate to a connector engagement apparatus including a detector configured to detect the "click" and provide a corresponding indicator to a user.

Figure 1:
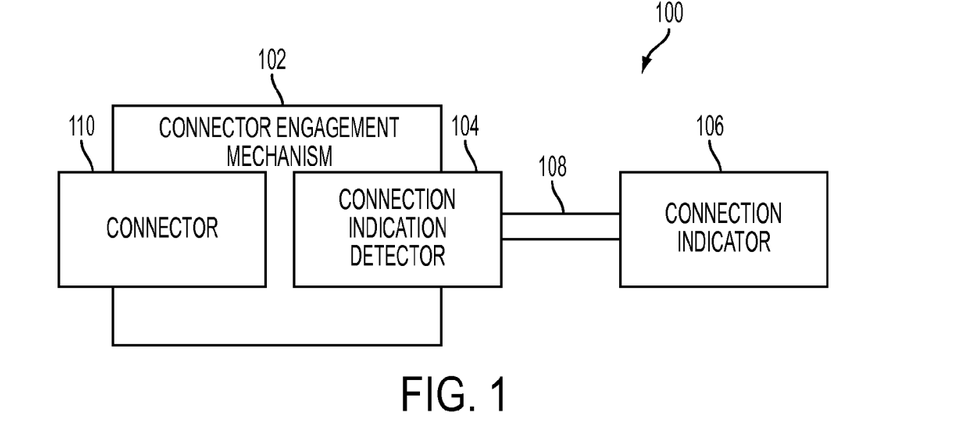
FIG. 1 illustrates a block diagram of a connector engagement apparatus according to one embodiment of the present disclosure.

FIG. 1 is a block diagram of a connection engagement apparatus 100 (also referred to as "apparatus 100", "connection apparatus 100", or "connection validation apparatus 100") according to an embodiment of the present disclosure. The apparatus 100 includes a connector engagement mechanism 102, a connection indication detector 104 located in, on, or near the connector engagement mechanism 102 and a connection indicator output unit 106 connected to the connection indication detector 104 to provide to a user an indication, based on an output from the connection indication detector 104, whether a connector 110 has been securely engaged with a connector interface, such as a receptacle.

In embodiments of the invention, the connector 110 may be attached to the end of a wire, tube, hose or other mechanism for transmitting power, data, or fluid. The connector interface to which the connector 110 attaches may be a fixed interface connected to, or recessed in, an object or structure, or the connector interface may also be connected to the end of a wire, tube, hose or other mechanism for transmitting power, data or fluid. In one embodiment, the connector 110 and connector interface have different structures that are physically complimentary to each other, such as a protrusion and a recess, to fit the connector 110 to the connector interface. In one embodiment, the connector 110 and the connector interface have identical physical structures including one or more of magnetic connectors, protrusions and recesses, that fit together to connect the connector to a connector interface. For example, each of the connector 110 and a corresponding connector interface may include a protrusion and a recess, and the connector 110 and the connector interface may fit together by arranging the connector 110 and the corresponding connector interface in a particular orientation with respect to each other.

A frame 108 is connected to the connector engagement mechanism 102 and provides a structure for a user to manipulate to control the placement of the connector 110. In embodiments of the present disclosure, the connector 110 may be any type of mechanical or electrical/mechanical connector that provides a noise or physical clicking sensation to indicate that the connector 110 has been securely connected with an interface, such as a receptacle. Examples of connectors include multi-fiber push-on/pull-off MTP/MPO connectors, Ethernet connectors and telephone connectors. The connectors may be connected to cords, lines or wires to connect the connector to a device. However, embodiments of the present disclosure are not limited to these particular connectors, and embodiments may include any type of mechanical connector or mechanical/electrical connector that includes a mechanism for generating a sound or sensation detectable by a user when the connector connects to a connector interface.

Examples of other connectors encompassed by the present invention include hydraulic fittings and pneumatic fittings, quick-connect fittings and other fittings for pipes, hoses and other tubes or channels to permit fluid flow. In these fittings, when a secure connection is not made, hydraulic fluid may leak, which may cause severe damage to a system.

A few examples of connectors have been provided for purposes of description only. However, embodiments of the present disclosure are not limited to these particular connectors, and embodiments may include any type of mechanical connector or mechanical/electrical connector that includes a mechanism for generating a sound or sensation detectable by a user when the connector connects to a connector interface.

The connector engagement mechanism 102 may be a fixed mechanism that is not actuated or it may be a movable mechanism for gripping the connector 110. Examples of fixed mechanisms include a rod that presses against a rear surface of the connector 110 and a socket that surrounds at least a portion of the connector 110. Examples of movable or actuating mechanisms include pliers, a hemostat or a clamp. The above fixed and movable mechanisms are provided only by way of example, and the connector engagement mechanism 102 may include any mechanism capable of engaging a connector 110 to cause the connector to securely connect with a connector interface.

In some embodiments, the connector engagement mechanism 102 is narrow compared to the connector 110. For example, the connector engagement mechanism 102 may have a width that is less than a width of the connector 110.

Examples of connector engagement mechanisms 102 that are narrow compared to a connector 110 include rods and pliers or clamps. Alternatively, the connector engagement mechanism 102 may have a width that is slightly larger than the connector 110 to hold the connector 110 in the connector engagement mechanism 102. Examples of connector engagement mechanisms 102 that may be wider than the connector 110 include a socket configured to contain therein the connector 110.

The connection indication detector 104 may include any type of sensor, film, membrane or any other sensing mechanism. In one embodiment, the connection indication detector 104 is a vibration sensor that detects a vibration of the connector 110, the connector engagement mechanism 102 or a connector interface to which the connector 110 is connected. In another embodiment, the connection indication detector 104 is a membrane that vibrates according to a sound made by the connector 110, the connector engagement mechanism 102 or a connector interface to which the connector 110 is connected. Acoustic waves may be transmitted via a tube to an amplification mechanism or ear inserts, such as with a stethoscope. In yet another embodiment, the connection indication detector 104 is a microphone, and a detection signal is transmitted electrically from the connection indication detector 104 to a speaker or earphones.

The connection indicator output unit 106 may be any device that provides an audio, visual or tactile indicator to a user based on a clicking sound detected by the connection indication detector 104. Examples of connection indicator output units 106 include speakers, openings to an acoustic channel, headphones, earbuds, one or more light-emitting diodes (LEDs), a liquid crystal display (LCD), a motor to provide a vibrating sensation, or any other device. In embodiments in which the connection indicator output unit 106 includes one or more LEDs, a single LED may turn on when a click is heard, a series of LEDs may turn on according to a volume of a sound (e.g. movement of the connector 110 may result in only one LED lighting up, while the click indicating a secure connection may result in three or four LEDs lighting up), words, letters or numbers may be generated, or any other visual indicator may be provided.

In other embodiments, the connection indicator output unit 106 is a separate device, such as a smartphone, tablet computer or other portable electronic device connected to the connection indication detector 104 and configured to provide one or both of an audio and a visual indicator when a connection is detected. For example, in one embodiment in which the connection indicator output unit 106 includes a portable computing device, a screen of the portable computing device may include symbols of a connector and a connector interface, such as a receptacle, being engaged with each other when the engagement click is detected by the connection indication detector 104.

The connection indicator output unit 106 may amplify a sound or vibration detected by the connection indication detector 104 or may convert the sound or vibration to another tactile output to make the sensing of the connection indication (such as the sound or vibration generated with a connector connects with an interface) easier for a user. For example, in a loud environment, converting a clicking connection sound to an LED display may help a user to detect a successful connection.

In some embodiments, the connection indicator output unit 106 is physically connected to the frame 108 via a wire. When the connection indicator output unit 106 is physically connected to the frame 108 via the wire, the connection indicator output unit 106 may be separable or detachable from the frame, such as by unplugging the wire or disconnecting the wire from a port. In other embodiments, the connection indicator output unit 106 is permanently or fixedly attached to the frame 108. For example, the connection indicator output unit 106 may be attached to the frame 108 via a mounting mechanism, such as screws, clamps, adhesives, bolts or any other mounting mechanisms. In such an embodiment, the connection indicator output unit 106 may be in a fixed position with respect to the frame 108, or the connection indicator output unit 106 may be rotatable with respect to the frame 108.

In one embodiment, the connection indication detector 104 includes a wireless transmitter to transmit signals indicating that a connector has engaged with a connector interface to a remote device. In other words, the connection indicator output unit 106 may be a remote device that is not physically attached to the frame 108. A user may manipulate the frame 108 to engage the connector 110 with a connector interface, and the connection indication detector 104 may provide a wireless signal to the connection indicator output unit 106 when a click is detected, indicating the secure engagement of the connector 110 with the connector interface. Examples of connection indicator output units 106 that are remote devices not physically connected to the frame 108 include wireless computing devices, such as smartphones and handheld devices, wireless earphones and any other wireless device configured to generate an audio, visual and/or tactile indicator to a user based on a detection signal from the connection indication detector 104.

In some embodiments, the frame 108 includes a user manipulation portion, such as one or more handles that are positioned to allow a user to grasp or squeeze the one or more handles to grab, move, push and pull the connector 110. The frame 108 may include both the connector engagement mechanism 102 and the handles or user manipulation portion. In some embodiments, the frame 108 is long and narrow relative to the connector 110. For example, in an embodiment in which the connector 110 has a length of between 1 cm and 2 cm, the frame 108 may have a length of between 15 cm and 30 cm. In other words, the frame may be at least an order of magnitude longer than the connector 110 to permit a user to grasp a user manipulation portion of the frame 108 to control a position of the connector 110.

Figure 2:
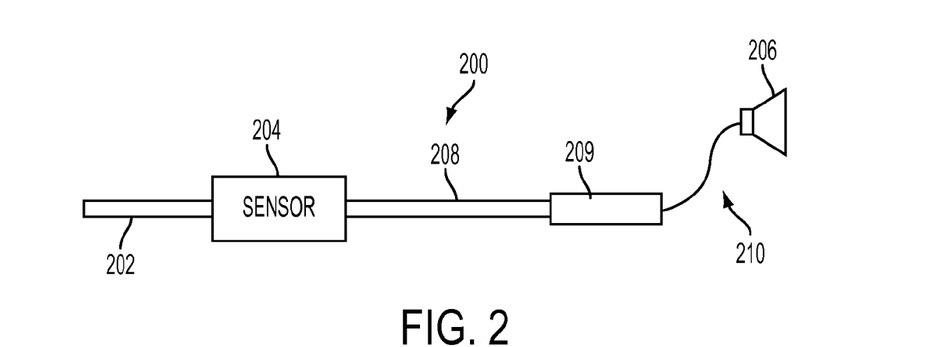
FIG. 2 illustrates a connector engagement apparatus according to an embodiment of the present disclosure.

FIG. 2 illustrates a connector engagement apparatus 200 according to one embodiment. The apparatus 200 includes a rod 202, a sensor 204 attached to the rod 202 or located in the rod 202, a frame 208 and a handle 209. While the rod 202 and handle 209 are illustrated as separate elements for purposes of description, these elements may be considered part of the frame 208. The apparatus 200 also includes an audio output device 206, such as a speaker. The audio output device 206 is connected to the frame 208 via a wire 210.

In the embodiment illustrated in FIG. 2, the rod 202 is configured to engage a rear surface of a connector to apply force to the connector based on a force provided by a user holding the handle 209. The user may accordingly apply the force to connect the connector to a connector interface. The sensor 204 may be an audio sensor, or a microphone, and may detect a click generated by the connector indicating a secure connection of the connector with the connector interface. The sensor 204 generates an electrical signal and transmits the electrical signal to the audio output device 206 via the wire 210.

The sensor 204 or audio output device 206 may include an amplifier to amplify the clicking sound to allow a user to hear the clicking sound. Alternatively, an amplifier may be provided in signal conditioning circuitry between the sensor 204 and the audio output device 206.

Figure 3:
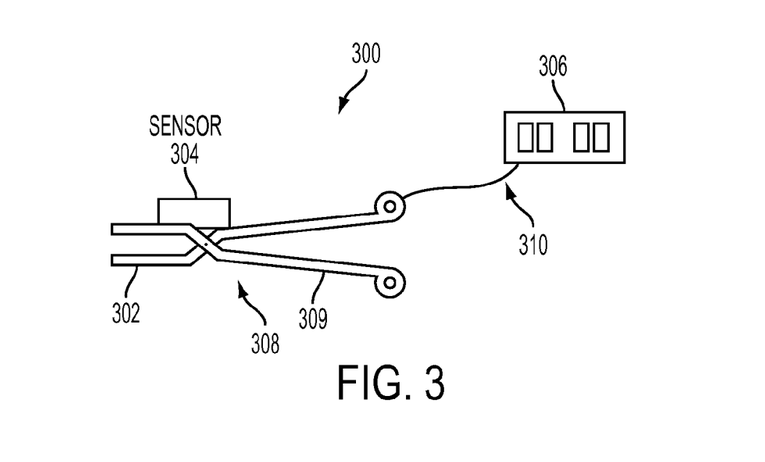
FIG. 3 illustrates a connector engagement apparatus according to another embodiment of the present disclosure.

FIG. 3 illustrates a connector engagement apparatus 300 according to one embodiment. The apparatus 300 includes a grasping portion 302, a sensor 304 attached to the grasping portion 302, and a handle 309. The grasping portion 302 and the handle 309 may make up the frame 308. The apparatus 300 also includes a visual output device 306, such as a light emitting diode (LED) display. The visual output device 306 is connected to the frame 308 via a wire 310.

In the embodiment illustrated in FIG. 3, the grasping portion 302 is configured to clamp onto opposing sides of a connector to apply force to the connector based on a force provided by a user holding the handles 309. The user may accordingly apply the force to connect the connector to a connector interface. The sensor 304 may be an audio sensor, or a microphone, and may detect a click generated by the connector indicating a secure connection of the connector with the connector interface. The sensor 304 generates an electrical signal and transmits the electrical signal to the visual output device 306 via the wire 210.

The sensor 304 may include an amplifier to amplify a signal corresponding to the clicking sound. Alternatively, an amplification circuit may be provided in the visual output device 306 or in signal conditioning circuitry between the sensor 304 and the visual output device 306.

Figure 4:
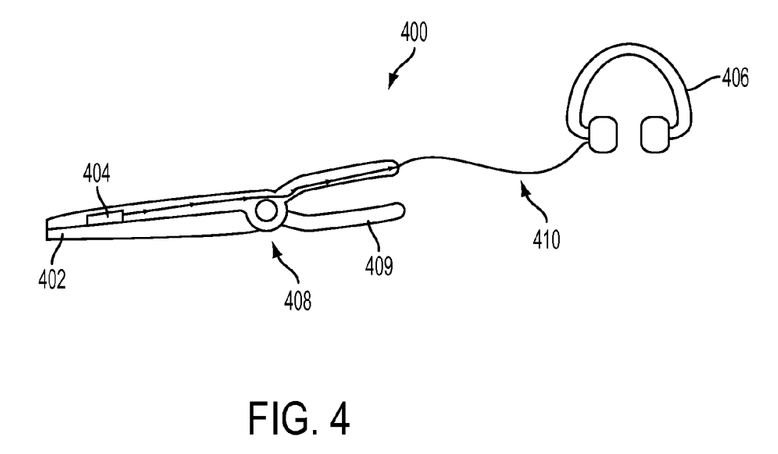
FIG. 4 illustrates a connector engagement apparatus according to another embodiment of the present disclosure.

FIG. 4 illustrates a connector engagement apparatus 400 according to one embodiment. The apparatus 400 includes a grasping portion 402, a membrane 404 attached to the grasping portion 402, and a handle 409. The grasping portion 402 and the handle 409 may make up the frame 408. The apparatus 400 also includes an audio output device 406, such as headphones. The audio output device 406 is connected to the frame 408 via a tube 410.

In the embodiment illustrated in FIG. 4, the grasping portion 402 is configured to clamp onto opposing sides of a connector to apply force to the connector based on a force provided by a user holding the handle 409. The user may accordingly apply the force to connect the connector to a connector interface. The membrane 404 vibrates based on acoustic waves generated by a click generated by the connector indicating a secure connection of the connector with the connector interface. The membrane 404 may be located on a grasping surface of the grasping portion 402, or a surface that faces or grasps the connector. The membrane 404 propagates the acoustic waves to the audio output device 406 via the tube 410.

Figure 5A:
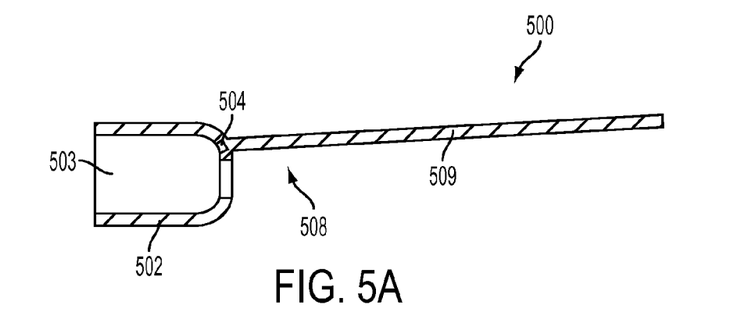
FIG. 5A illustrates a connector engagement apparatus according to another embodiment of the present disclosure.

FIG. 5A illustrates a connector engagement apparatus 500 according to one embodiment. The apparatus 500 includes a connector receiving portion 502 defining a cavity 503 having a size corresponding to the size of a particular type of connector. A sensor 504 is embedded in the connector receiving portion 502. The sensor 504 may be embedded in a receiving surface of the receiving portion 502, or a surface that faces or contacts a connector when the connector is located in the receiving cavity 503. The apparatus 500 also includes a handle 509. The connector receiving portion 502 and the handle 509 may make up the frame 508. In FIG. 5A, a connection indicator output unit is omitted for purposes of description only.

Figure 5B:
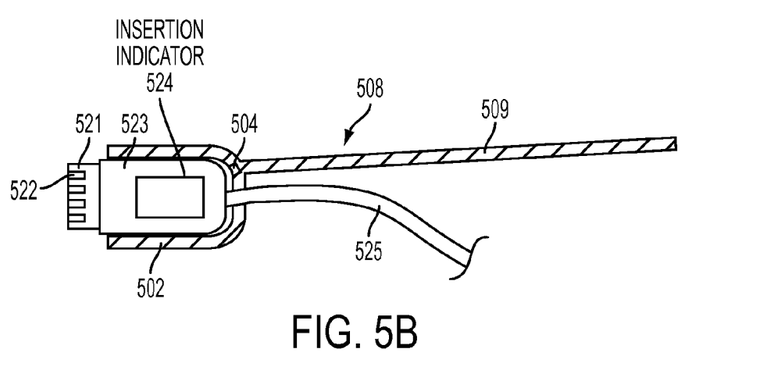
FIG. 5B illustrates a connector engagement apparatus with a corresponding connector according to an embodiment of the present disclosure.

As illustrated in FIG. 5B, the connector receiving portion 502 is configured to receive a connector 523 in the cavity 503. A connection end 521 of the connector 523 may include electrical leads 522. The connector 523 may include a connection indicator 524, such as a spring or other directionally-biased structure that is configured to generate one of a distinctive vibration and a distinctive sound, such as an audible clicking sound, when the connector 523 is securely engaged with a connector interface.

While FIGS. 2-5B provide some example embodiments, the scope of the present invention is not limited to the embodiments described. For example, a connector engagement apparatus having the form of a rod may utilize a microphone, a membrane or any other sensor and may output an audio, visual or tactile indicator to a user. Similarly, connector engagement apparatuses having grasping mechanisms, connector-receiving cavities or any other configurations may utilize any sensing mechanism and any user output mechanism including sound and vibration sensors and audio, visual and tactile outputs to a user.

Figure 6:
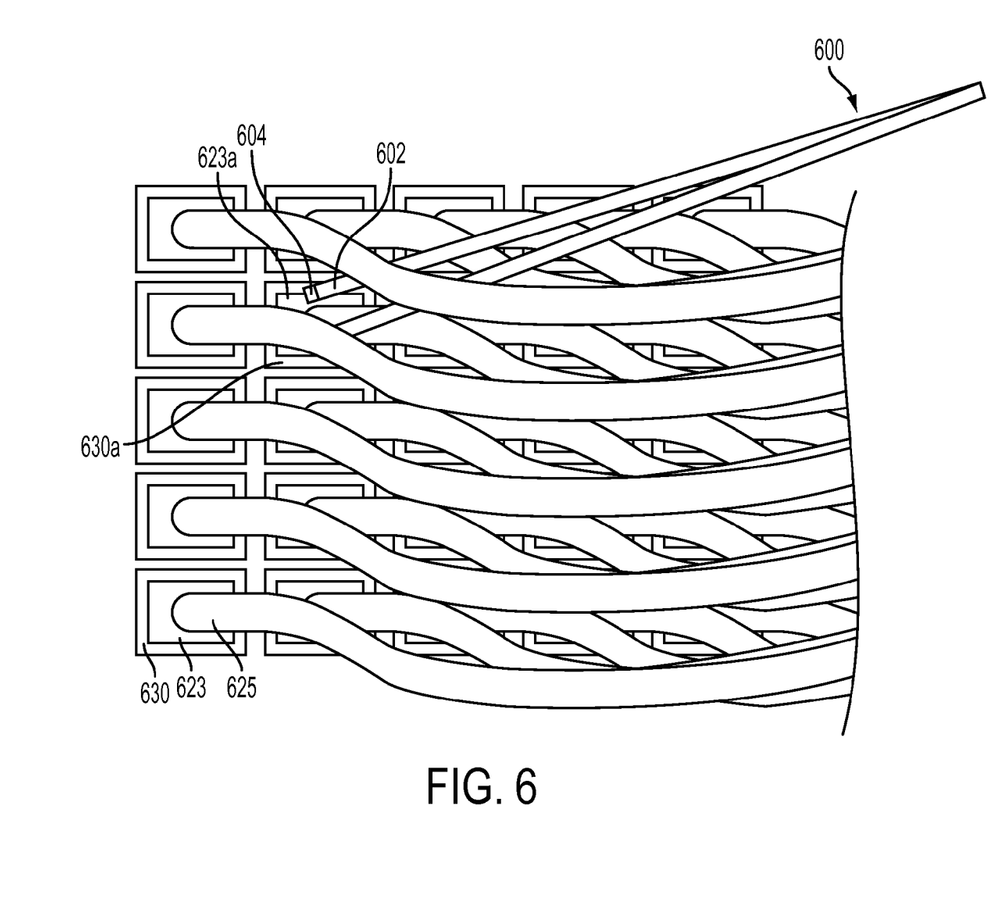
FIG. 6 illustrates a connector engagement apparatus and connector array according to an embodiment of the present disclosure.

FIG. 6 illustrates an example a connector engagement apparatus 600 in use. In some electrical and computer systems, arrays of connectors 623 are provided, making access to the connectors 623 difficult. Each connector 623 may be situated at the end of a wire or cable 625 and may be configured to fit into, and electrically and/or mechanically connect with, a connector interface 630, such as a receptacle 630. In addition, in noisy environments, it may further be difficult to discern a connection sound or vibration generated by one of a receptacle 630 and the connector 623 indicating a secure connection of the connector 623 with the receptacle 630.

As illustrated in FIG. 6, the connector engagement apparatus 600 includes a connector engagement mechanism 602 configured to contact the connector 623*a* and to apply force to the connector 623*a* to cause the connector 623*a* to securely connect with the receptacle 630*a*. A connection indication detector 604 is located on the connector engagement mechanism 602 and detects one of a vibration and a sound, such as a clicking sound, generated by one of the receptacle 630*a* and the connector 623*a* to indicate that a secure connection has been made. The connection indication detector 604 may then transmit a signal or acoustic waves to a connection indicator output unit (not shown) to notify a user that a secure connection has been detected.

In the above embodiments, springs or spring-biased mechanisms have been described as examples of connection indicators 524. However, connection indicators are not limited to the examples described above. An connection indicator may correspond to any structure on a connector, a connector interface configured to connect to the connector, or a connector engagement mechanism that is configured to move the connector into contact with a connector interface, where the connection indicator provides an indication to a user of a secure or stable connection of the connector to the connector interface. A clicking sound and a clicking or sudden fastening sensation are provided as examples of indications of secure or stable connections, but any indication that is detectable by a user may be used and detected according to embodiments of the disclosure.

Figure 7:
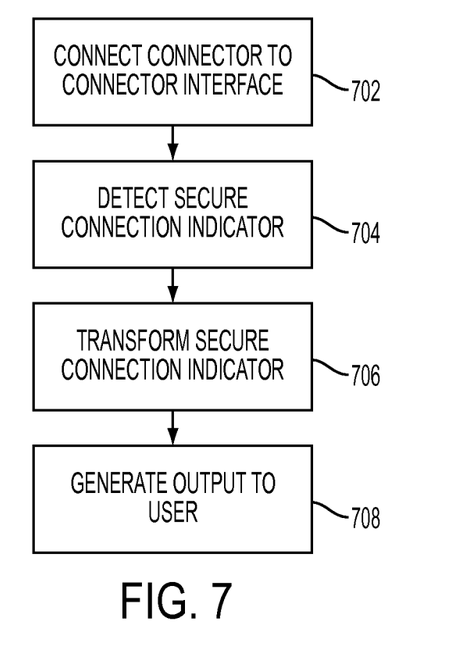
FIG. 7 is a flowchart illustrating a method according to an embodiment of the present disclosure.

FIG. 7 is a flowchart illustrating method according to an embodiment of the disclosure. In block 702, a connector is connected to a connector interface using a connection apparatus controlled by a user. The connector may be a mechanical connector and may also include electrical leads or connections. The connector interface may be any type of interface capable of securely connecting with the connector, such as a receptacle. In one embodiment, the connector is a connector of a communications line and the connector interface is a receptacle configured to transmit communication signals to or from the connector.

In block 704, a connection indication detector detects a secure connection indicator. The secure connection indicator may be one of a vibration and a sound generated by the connector or the connector interface to indicate that a secure connection has been made. In one embodiment, the secure connection indicator is a connection validation sound generated by the connector based on the connector being connected to the connector interface.

In block 706, the secure connection indicator is transformed. For example, transforming the secure connection indicator may include amplifying acoustic signals, propagating acoustic signals via a membrane, changing acoustic signals to electrical signals transmittable via a wire, or changing acoustic signals to wireless electrical signals. Similarly, transforming the secure connection indicator may include transforming vibrations of the connector or the connector interface.

In block 708, at least one of an audio, a visual, and a tactile output is provided to a user based on the transformed secure connection indicator. For example, an amplified clicking sound may be output via an opening in a tube configured to propagate acoustic signals, a speaker may generate a clicking sound, earphones may generate a clicking sound, a light-generating device may generate a light signal, or a tactile device may vibrate or provide another tactile sensation corresponding to the secure connection indicator.

Embodiments of the present disclosure encompass connection validation mechanisms and methods that detect and transform a connection indicator, such as a clicking sound or vibration, and provide the transformed connection indicator to a user via one or more of an audio, visual or tactile output unit or device. The connection validation mechanisms may amplify the connection indicator or convert the connection indicator to another sensory output. Accordingly, users may detect secure connections of connectors and connector interfaces, even in noisy environments and environments in which multiple connectors are connected in close proximity to each other, which makes access to the connectors difficult.

Embodiments encompass apparatuses that engage a connector with pliers, a rod and a connector-securing cavity. A connection indication may be connected with a microphone or vibration sensor. In one embodiment, a connection indication detector is a membrane that vibrates based on sound, and acoustic signals are transmitted from the membrane to an opening in an earpiece of a user.

Embodiments include an electronic display that is electrically connected to a connection indication detector, and which generates a visual indicator based on the detection of the connection indicator. The electronic display may be an LED display or an LCD display, for example.

In one embodiment, a connection indicator output unit is wirelessly connected to a connection indication detector, and the connection indication detector is configured to transmit a wireless electrical signal to the connection indicator output unit based on the detection of the at least one of the sound and the vibration by the connection indication detector.

In one embodiment, the connector engagement mechanism is a rigid mechanism configured to apply a force to the connector, and the connection indicator output unit is isotropically movable relative to the engagement mechanism. In one embodiment, a connector engagement mechanism includes an engaging surface configured to physically engage the connector to connect the connector to a connector interface, and a connection indication detector is located either on the engaging surface or recessed in the engaging surface.

In one embodiment, a connector includes a connection validation mechanism configured to generate a clicking sound based on the connector being securely connected to a connector interface, a connection indication detector is configured to detect the clicking sound, and a connection indicator output unit is configured to provide at least one of an audio, a visual and a tactile indicator to a user based on the detection of the clicking sound by the connection indication detector.

In one embodiment, a connection indicator output unit includes an audio output to a user, at least one of the connection indication detector and the connection indicator output unit is configured to amplify the clicking sound, and the connection indicator output unit is configured to output the amplified clicking sound.

In one embodiment, a user manipulation portion is located at one end of a frame of a connection validation apparatus, and a connector engagement mechanism is located at an opposing end of the frame of the connection validation apparatus.

Embodiments include detecting and amplifying a connection validation sound. In some embodiments, generating an audio output includes generating an amplified audio output to a user by transmitting the transformed connection validation sound in the form of acoustic waves to an earpiece via a tube. In one embodiment, a connection validation sound is transformed by converting acoustic waves to an electrical signal transmittable via a wire to at least one of an audio, visual and tactile output device.

In one embodiment, a connection validation sound is transformed by converting acoustic waves to wireless electrical waves, and generating audio, visual or tactile output includes transforming the wireless electrical waves to one of a sound, light visible by a user, and a motion.

The flowchart and block diagrams in the Figures illustrate the architecture, functionality, and operation of possible implementations of apparatuses, systems, methods according to various embodiments of the present disclosure. It should be noted that embodiments of the disclosure encompass apparatuses, systems and methods that include additional blocks or features.

The terminology used herein is for the purpose of describing particular embodiments only and is not intended to be limiting of the invention to the particular embodiments described. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosed embodiments. Many modifications and variations will be apparent to those of ordinary skill in the art without departing from the scope and spirit of the embodiments of the present disclosure.

While preferred embodiments have been described above, it will be understood that those skilled in the art, both now and in the future, may make various improvements and enhancements which fall within the scope of the claims which follow.

What is claimed is:

1. A method of validating a connection, comprising:
   connecting a connector to a connector interface using a connection apparatus controlled by a user;
   detecting, by a connection indication detector installed directly on, and integrated with, the connection apparatus, a connection validation based on at least one of a sound and a vibration generated by the connector, the connection validation corresponding to a secure connection of the connector and being generated in response to physically connecting the connector directly to the connector interface;
   transforming, by the connection indication detector integrated with the connection apparatus, the connection validation sound, generated in response to the physical connection between the connector and the connector interface, to generate a transformed connection validation sound that is different from the connection validation; and
   generating an indication different from the connection validation sound, the indication including at least one of an audio, a visual, and a tactile output to a user in response to detecting the transformed connection validation sound, the indication being an electrical detection signal indicating that the connector is securely connected with the connector interface in response to detecting at least one of the sound and the vibration.

2. The method of claim 1, wherein said transforming the connection validation sound further includes amplifying the connection validation sound.

3. The method of claim 2, wherein said generating the at least one of the audio, visual and tactile output further includes generating an amplified audio output to a user by transmitting the transformed connection validation sound in a form of acoustic waves to an earpiece via a tube.

4. The method of claim 1, wherein said transforming the connection validation sound further includes converting acoustic waves to an electrical signal transmittable via a wire to at least one of an audio, visual and tactile output device.

5. The method of claim 4, wherein said generating the at least one of the audio, visual and tactile output further includes generating a visual output by turning on at least one light of a visual output device.

6. The method of claim 1, wherein said transforming the connection validation sound further includes converting acoustic waves to wireless electrical waves, and
   said generating the at least one of the audio, visual and tactile output further includes transforming the wireless electrical waves to one of a sound, light visible by a user, and a motion.

* * * * *